United States Patent [19]
Brener et al.

[11] Patent Number: 5,894,125
[45] Date of Patent: Apr. 13, 1999

[54] NEAR FIELD TERAHERTZ IMAGING

[75] Inventors: Igal M. Brener, Eatontown; Martin C. Nuss, Fair Haven, both of N.J.

[73] Assignee: Lucent Technologies Inc., Murray Hill, N.J.

[21] Appl. No.: 08/912,631

[22] Filed: Aug. 18, 1997

[51] Int. Cl.⁶ ............................................. G01N 21/17

[52] U.S. Cl. ............................ 250/330; 250/341.1

[58] Field of Search ............................... 250/338.1, 330, 250/493.1, 341.1

[56] References Cited

U.S. PATENT DOCUMENTS

| | | | |
|---|---|---|---|
| 5,623,145 | 4/1997 | Nuss | 250/330 |
| 5,710,430 | 1/1998 | Nuss | 250/330 |
| 5,729,017 | 3/1998 | Brener et al. | 250/338.1 |
| 5,789,750 | 8/1998 | Nuss | 250/330 |

*Primary Examiner*—Constantine Hannaher
*Assistant Examiner*—Darren M. Jiron

[57] ABSTRACT

A THz imaging system with the emitter region of the THz generator designed so that the sample to be analyzed is placed in the near field of the generator allows radiation to impact the sample without intervening optics.

14 Claims, 2 Drawing Sheets

NEAR FIELD TERAHERTZ IMAGING

FIELD OF THE INVENTION

This invention relates to far infra-red pulsed beam devices operating in the $10^{10}$ to $10^{13}$ Hz frequency regime (THz radiation), and more specifically to systems for imaging and spectroscopy using terahertz (THz) radiation in the near field.

BACKGROUND OF THE INVENTION

Far infra-red pulsed beam devices operating in the terahertz frequency range have been described in various forms in the prior art. Devices have been used in time resolved infrared spectroscopy to characterize a variety of properties of solid state materials such as refractive index, photoconductivity, absorption, and dispersion.

Recent advances in terahertz beam generation can be attributed to optoelectronic interactions in semiconductor photoconductors. The advantage of this mechanism is that the radiation produced by this interaction can be radiated into free space. The beam can be steered using conventional optics to direct it onto samples for analysis, or imaging, and refracted or reflected to a photodetector operating on the same principle as the generator. A more thorough description of such a device is given by Smith et al, "Subpicosecond Photoconducting Dipole Antennas", *IEEE Journal of Quantum Electronics*, Vol. 24, No. 2,, pp. 255–260, February 1988. The device described by Smith et al uses a coplanar stripline terminating in a dipole antenna consisting of a small electrode gap formed over intrinsic silicon on sapphire. The electrode gap produces the high field photoconductive region. The pump beam was a mode locked dye laser pumped with an argon laser and operating with a pulse duration of 120 fs at 620 nm.

Another terahertz device is described by Van Exter et al in "Characterization of an Optoelectronic Terahertz Beam System", *IEEE Transactions on Microwave Theory and Techniques*, Vol. 38, No. 11, pp. 1684–1691, November 1990. Van Exter et al describe a device that uses a dipole antenna formed in the middle portion of a stripline. The substrate forming the photoconductive region in their device is also silicon on sapphire and they also use a colliding-pulse mode-locked dye laser as the pump source.

The terahertz generators/detectors in all of these devices is relatively simple in structure. Basically they comprise a semiconductor substrate with electrodes on the substrate and a small gap between the electrodes. With an appropriate DC bias applied to the electrodes, a field is established across the gap which produces a small high field photoconductor region near the surface of the semiconductor in the electrode gap. When this region is excited by fast pulses of light, rapid changes in conductivity occur. In the presence of the DC electric field these changes in conductivity result in ultrafast pulses of electric current through the dipole forming the gap, and equally ultrafast bursts of electromagnetic radiation are emitted from the gap region. Much of this radiation is emitted into the substrate, and since it has a photon energy well below the direct bandgap of the semiconductor, it can be collected by suitable lens arrangements on the obverse side of the semiconductor. The radiated beam can be collimated and focused using suitable mirrors, and can be detected by a device operating in a mode in reverse to that just described.

These THz devices were considered potentially useful in high speed pulse generators, high speed switching devices for communications and related applications, and in far infrared spectroscopy studies of different materials.

The potential usefulness of THz radiation for spectroscopy was later reported by Ralph et al in "Terahertz Beams: Generation and Spectroscopy", *Mat. Res. Soc. Symp. Proc.*, Vol. 261, 1992, pp. 89–100, 1992. Much of this paper deals with the design and operation of the THz generator. Ralph et al analyzed the effect of the semiconductor properties on the electric field profile between the electrodes forming the emitter gap. They found that semi-insulating semiconductors produce enhanced field profiles. The desired semi-insulating property may be obtained through choice of a material with high trap density, or traps may be created in a normal semiconductor by ion beam damage. The device of Ralph et al used a semi-insulating substrate (GaAs) and the high field region was formed by relatively widely spaced (80 μm) parallel electrode strips. The THz radiation produced by the apparatus described by Ralph et al was used to experimentally demonstrate THz time domain spectroscopy.

A more recent development in this technology was the proposal and demonstration of T-ray imaging by Hu and Nuss and reported in "Imaging with terahertz waves", *Optics Letters*, Vol. 20, No. 16, pp 1716–1718, August 1995. T-rays here refers to THz waves, and imaging with these waves is based on the fact that dielectric materials are quite transparent to this radiation, whereas water rich materials and metals are not. The maximum spatial resolution obtained in this work was limited by diffraction theory of far-field optics which in this case translates to roughly 150–400 μm.

Following these published results interest increased in applications requiring effective imaging using THz beams. Pulsed THz devices have been used to characterize a variety of properties of solid state materials such as refractive index, photoconductivity, absorption, and dispersion.

Terahertz radiation imaging (T-ray imaging) shows promise in a variety of analytical applications such as chemical mapping, and a host of commercial applications such as safe package inspection, industrial process control, food inspection, biology and medicine. As radiation sensors, these devices are effective for analysis of solids, liquids or gases. Analysis of gases is particularly effective since gases have characteristically strong absorption lines in the THz frequency range. Accordingly, these devices can be used effectively for environmental studies and environmental monitoring.

Although these systems are characterized as T-ray imaging systems, they typically are applications that do not require high spatial resolution. It was recognized early that THz beams inherently have low spatial resolution, typically several hundred microns. Consequently their usefulness in many analytical applications, particularly in several sophisticated forms of time domain spectroscopy, requiring high spatial resolution, has thus far been limited.

In a recent advance in THz radiation imaging technology, near field imaging was pursued to overcome the resolution limitations of prior THz systems. Near field imaging allows spatial resolution below the wavelength of the radiation, i.e. sub-wavelength radiation. As described earlier, in a typical prior art THz generating device the emitter gap region is illuminated with a pump laser incident on the emitter gap surface, and far field radiation is emitted from the back side of the device substrate. This far field radiation can be converted to near field radiation using a small aperture converter device. This approach has been used successfully to produce scanning wavelengths well below the far field range. See e.g. S. Hunsche et al, "Near-Field THz Imaging", OSA Trends in Optics and Photonics Series (TOPS) Volume on Ultrafast Electronics and Optoelectronics (UEO TOPS 97').

In the near field system used by Hunsche et al, the near field converting device was a tapered metal tube, analogous to the tapered fibers used in near-field. scanning optical microscopes, and the tapered tube was used to aperture a conventional THz source beam to a spot smaller than the radiation wavelength. The tube was formed by electroplating a small conical aluminum tip with a Ni/Cr alloy, and polishing the tip to produce small circular apertures of the order of 50–100 µm. This aperture diameter corresponds to λ/3 for a T-ray frequency of 1 THz. The THz beam was focused into the 2 mm opening of the tapered tube using off-axis paraboloid mirrors. While this technique has been successful, it requires somewhat complicated apparatus, and is lossy due to the multiple interactions of the THz beam with the beam collimating, steering, and near field converter surfaces.

BRIEF STATEMENT OF THE INVENTION

We have devised a simpler and more efficient near field THz imaging system. It is based on special design of the THz generator to provide access directly to the primary near field of the THz source. In this system much of the beam steering optics are eliminated, as well as the tapered tube aperturing device. It allows placement of the sample element being scanned directly into the near field of the THz emitter. The THz radiation impacts the sample without any optics intervening between the emitter and the sample, thus providing optimum beam flux to the sample.

DETAILED DESCRIPTION

Figure 1:
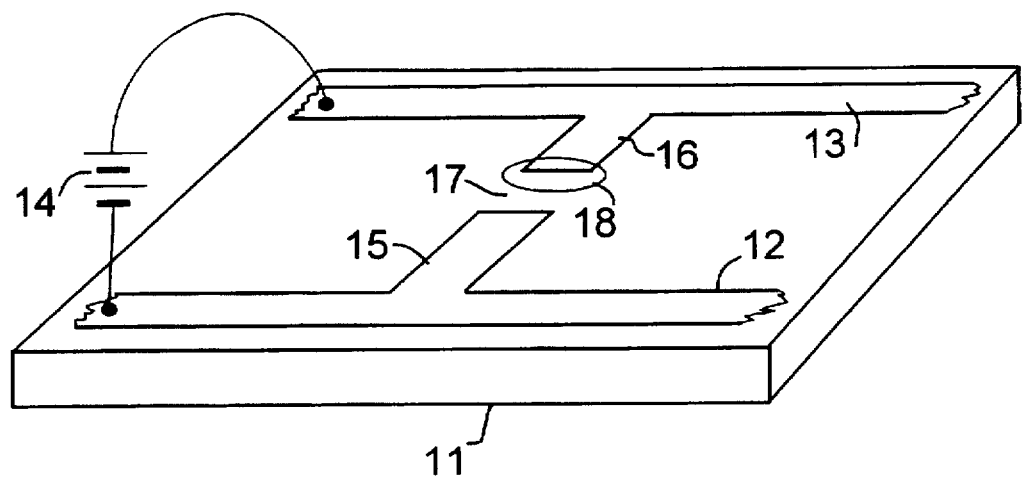
FIG. 1 is a schematic representation of a typical terahertz generator/detector.

With reference to FIG. 1, the essential elements of a terahertz generator/detector according to the invention are shown in schematic form. Semiconductor substrate 11 is shown with strip electrodes 12 and 13 interconnected with DC bias 14. The dipole members 15 and 16 form an electrode gap 17 which is the active site of the device. Laser spot 18 from the pump laser (not shown) is incident on a portion or all of the gap. Here the pump laser is shown incident on the portion of the gap adjacent the anode of the gap.

The pump source is typically a femtosecond pulse laser operating at a wavelength of 400 nm to 2000 nm and a pulse duration of 10 picoseconds or less. Alternatively it comprises two CW lasers tuned slightly apart and mixed together to give a difference mixing wavelength.

In the usual pump arrangement described in the prior art the pump beam is incident on the top surface of the semi-conductor (as it appears in FIG. 1). The generated THz signal radiates in all directions but a large fraction is emitted into the substrate 11 and is collected from the backside of the substrate. Typically the backside of substrate 11 is equipped with a collimating device, e.g. a high resistivity silicon hyperhemispherical substrate lens (not shown). It is significant to note that the THz radiation emitted from the backside of the substrate is already in the far field, so a far field to near field radiation converter device is required to produce sub-wavelength radiation. Such an approach was followed by Hunsche et al. as described above.

The material forming the photoconductor layer may be selected from a wide variety of semiconductor materials. Silicon and gallium arsenide are most commonly used. The semiconductors may be intrinsic or lightly doped. They may also have high trap densities to reduce carrier lifetime and enhance the electric field across the emitter gap 17.

The runners 12 and 13 typically comprise metallization patterns formed by photolithography. The electrode material may be e.g. aluminum. titanium-platinum, titanium-gold, chromium. Selection is not critical. Typical widths for these runners is 10–30 µm. The DC bias 14 is typically 5–1000 volts depending on the size of the gap 17. Typical gap lengths, i.e. the spacing between the dipoles lines 15 and 16, is 3–100 µm. The gap width is comparable. The nominal size of the gap may be chosen to correspond to the aperture of the pump beam. Since larger pump beams give wider terahertz beam output, it is generally desirable to have the dimensions of gap 17 at least as large as the pump beam. The gap may be larger than the beam, as is the case in the devices described by Ralph et al.

While the descriptions of the prior art devices envision a single pump beam, multiple pump beams may be used. In a preferred embodiment the pump beam may be directed to the gap by an optical fiber. Also the terahertz pulsed output beam may be collected using a device analogous to an optical fiber functional in the far infrared.

Figure 2:
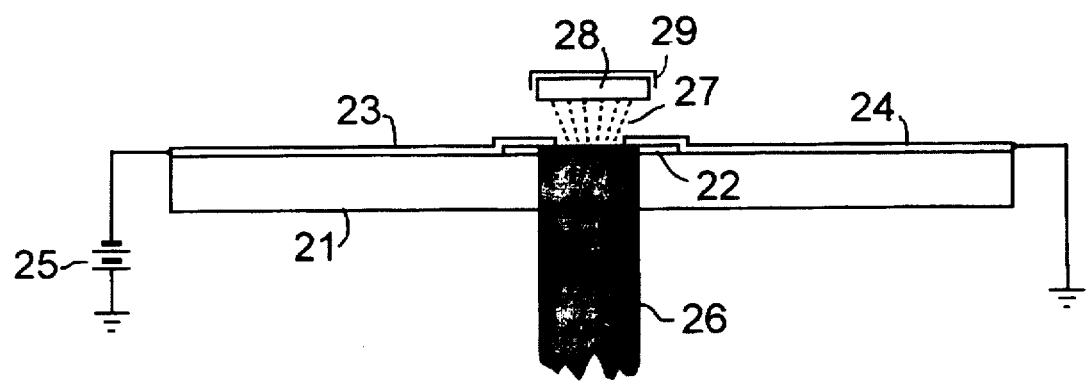
FIG. 2 is a schematic view of one embodiment of a near field THz imaging system according to the invention.

A THz generator according to the present invention, with near field imaging, is shown in FIG. 2. Substrate 21 is sapphire with a thickness of 100–500 µm. The substrate is polished on both sides to provide an optically flat interface. A semiconductor film is shown at 22 and constitutes the photoconductor layer of the THz generator. The semiconductor film is preferably silicon but as indicated above a variety of materials could be used. Silicon on sapphire (SOS) is a preferred choice for the invention since the technology for producing SOS films is well established, and the dielectric constants of these materials are matched within approximately 10%, thus providing efficient optical interfaces. However, other combinations can be used, such as other semiconductors deposited on top of substrates transparent to the laser beams.

The crystal perfection of the film 22 is not critical. It may range from highly ordered, even epitaxial, to amorphous. The film is preferably intrinsic or high resistivity, with a resistivity of at least 10 Ω cm. In the case of silicon on sapphire, the silicon film is preferably radiation damaged with e.g. 1–5 MeV argon atoms to reduce the carrier lifetime of the silicon and increase the voltage across the emitter gap. The thickness of the silicon film may be in the range 0.05–3.0 µm, and preferably 0.1–1.0 µm. The DC bias source is shown at 25. The geometry of the gap may be constructed according to the teachings in copending patent application Ser. No. 08/656,000. now U.S. Pat. No. 5,729, 017 filed May 31, 1996, and incorporated by reference herein. Techniques for enhancing the THz radiation intensity, and for localizing the radiation output, are described in that application.

According to the invention, the substrate 21 in FIG. 2 is chosen to be transparent to the laser pump radiation beam 26, so that the emitter gap can be illuminated with the laser pump beam from the backside of the device. This is an essential feature of this embodiment of the invention as it provides access to the near field region at the emitter gap. As described earlier, in most conventional THz generators, the emitter gap region is illuminated from the front side of the device, since the pump laser wavelength is deliberately chosen so that it is strongly absorbed by the photoconductor material. While pumping the emitter gap from the backside of the device has been done in some early THz generator experiments, conventional THz imaging systems employ front side pumping. This means that the radiation emitted from the emitter gap is already in the far field as it emerges from the backside of the substrate. Thus a far field to near field converting device would normally be required to produce useful near field radiation. However, with backside pumping of the emitter gap according to the invention, the sample holder 29 and the sample 28 to be scanned can then be located in immediate proximity to the emitter gap, i.e. directly in the near field, to receive the subwavelength THz radiation schematically represented at 27. The spatial resolution at the surface of the sample 37 is substantially less than the far field resolution, i.e. the THz wavelength, typically several hundred microns.

As mentioned, the appropriate pump wavelength is one which is strongly absorbed by the photoconductor. Typical semiconductor photoconductor materials have strong absorption bands in the wavelength range of 0.4–20 microns, and for silicon 0.4–1.1 microns. Selection of the substrate material in this embodiment is dictated by the choice of the photoconductor material since the substrate should be substantially transparent to the wavelength used to pump the photoconductor. Substantially transparent, in the context of the invention, means that at least 50% of the laser pump radiation that is incident on the backside of the substrate is transmitted through the transparent portion of the substrate to the photoconductor layer 22. Also, to effectively pump the photoconductor, the material of the photoconductor should absorb at least 10% of the pump radiation transmitted through the substrate material.

For the practice of the invention the following specific approach is recommended. The device structure is that shown schematically in FIG. 2. The substrate 21 is sapphire, and the semiconductor layer 22 is <100> oriented, 100 Ω cm silicon, deposited on the sapphire substrate by conventional CVD. The carrier lifetime of the silicon is adjusted by radiation damage using 2 MeV argon ions at an ion beam current of 250 nA and fluence of $3 \times 10^{15}$ cm$^{-2}$. The deposited silicon is lithographically patterned (either before or after the damage step) to form the photoconductor pad 22. The dimensions of the pad are not critical. A 50 micron square would be appropriate. In principle, the silicon layer can cover the substrate 21, but it is preferably confined to the emitter gap region to reduce the potential for noise coupling between the conductors at regions remote from the emitter gap. This is of concern if the conductor pattern (not shown) is in a stripline configuration as is typical in these devices.

The silicon pad and the metallization patterns can be fabricated using conventional lithography. A suitable width for the electrodes 23 and 24 is approximately 10 µm wide and the spacing between them approximately 70 µm. Appropriate metallization materials are: Al, Ti—Au, Ti—Pd—Au, (800A Au—Ge, 200A Ni, 200A Ti, 2000A Au), or (100A Ni, 800A Au—Ge, 200A Ni, 3000A Au). The pump beam was a mode-locked Ti-sapphire pulsed laser with radiation at 780 nm and pulses at 150 fs.

The pump beam is incident on the back side of the substrate through a 20X objective with a spatial resolution of ~2 µm. The DC bias can be 10–30 volts (corresponding to fields up to 50 kV/cm). The THz radiation from the sample was collected with a pair of off-axis paraboloids (not shown). In our demonstration, the near field proximity (spacing between the sample surface and the surface of the emitter) of the sample was 10 microns, and the spatial resolution was 100 microns.

Access to the emitter gap region can be further accommodated by etching a mesa into the transparent substrate, and forming the epitaxial photoconductor on the mesa. This structure is conveniently fabricated by forming the epitaxial silicon layer on a planar sapphire substrate, then masking the epitaxial layer and etching through the masked portion of the silicon layer, and continuing the etch through a portion of the sapphire substrate. Plasma etch techniques to accomplish this are well known. This mesa structure can be used to form a miniature THz generator device that can be mounted on the end of an optical fiber to produce a convenient probe.

Figure 3:
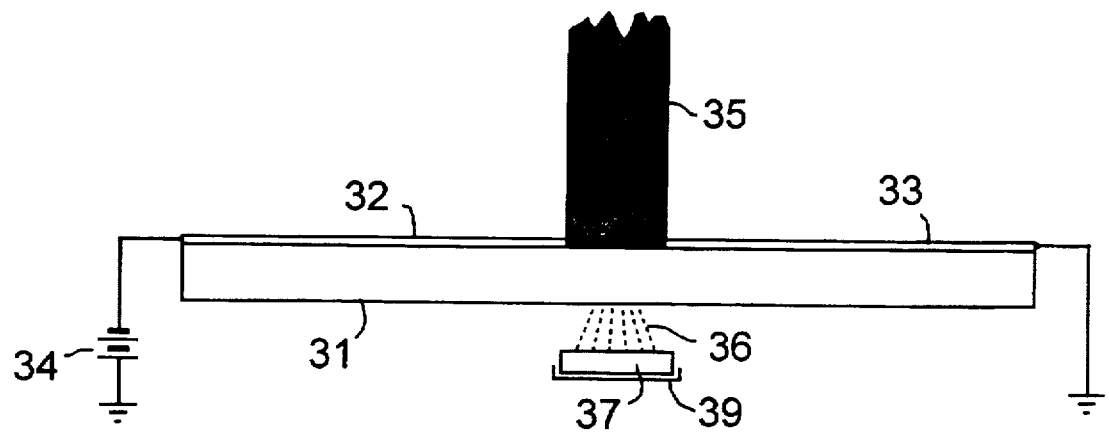
FIGS. 3 and 4 are a schematic views of alternative near field THz imaging systems according to the invention.
Figure 4:
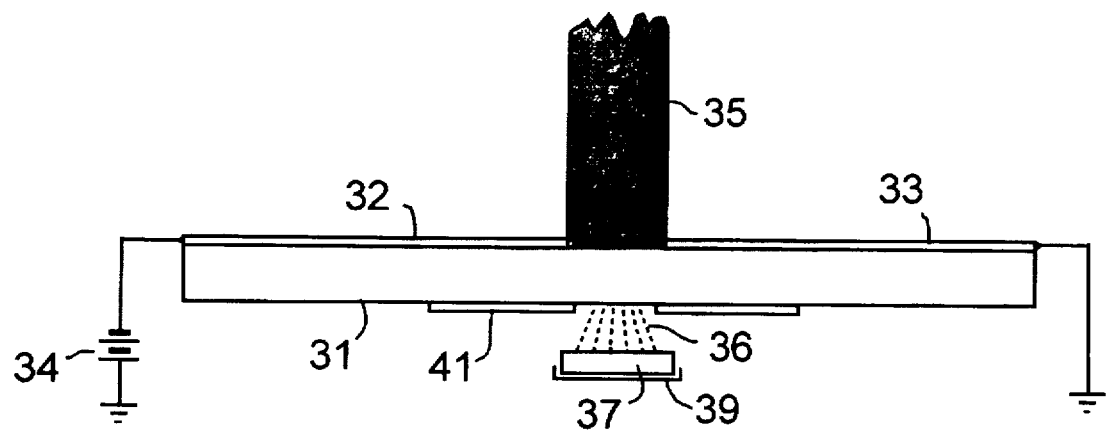

An alternative THz generator with near field access is shown in FIGS. 3 and 4. In this general embodiment the substrate 31 is thinned to produce a substrate thickness substantially less than the far field wavelength of the THz radiation, e.g. less than 200 microns, and preferably less than 100 microns. The electrodes forming the emitter gap are shown at 32 and 33 in FIG. 3, with DC bias shown at 34. In this embodiment the emitter gap between the electrodes is illuminated by the pump laser beam 35 from the front side of the device. The THz radiation 36 propagates through the substrate 31 and is emitted into the free space at the backside of the thinned substrate. The substrate is sufficiently thin that the free space region at the backside, where sample holder 39 and the sample 37 is mounted for scanning, is well within near field proximity of the emitted THz radiation. For this embodiment the preferred substrate material is low temperature LT-GaAs grown at ~250° C. and later annealed for one minute at 600° C., although other semiconductors should work equally well.

In FIG. 4, the radiating surface at the backside of the substrate 31 is shown with a pinhole 41. The pinhole may be formed of metallization similar to that used for electrodes 32 and 33, or other suitable material such as gold that is opaque to the THz radiation. The pinhole serves to ensure that the radiation reaching the sample 37 has a spatial dimension given by the pinhole and not by the terahertz radiation. The pinhole diameter should be substantially less than the nominal THz wavelength, i.e. less than 200 microns, and preferably less than 100 microns. Experimentally, a pinhole with a 50 micron diameter was used.

The term near field proximity as used in this specification is defined as within a distance less than the far field wavelength of the THz radiation, i.e. less than the nominal wavelength of the THz radiation. When the sample is located within near field proximity of the emitter gap the space between the sample and the emitter gap is void space. The THz beam can be used in a normal atmosphere, or can be enclosed in a nitrogen or inert atmosphere to reduce potential contamination and absorption from water vapor, etc.

Also for the purpose of defining the invention the substrate is characterized as having a surface side, and a backside. By definition a substrate is a quadrangular body with a thickness less than the length or width. The thus defined major planes of the substrate comprise the surface and the backside.

Various additional modifications of this invention will occur to those skilled in the art. All deviations from the specific teachings of this specification that basically rely on the principles and their equivalents through which the art has been advanced are properly considered within the scope of the invention as described and claimed.

We claim:

1. A system for imaging objects using far infra-red pulsed radiation in the frequency range of $10^{10}$ to $10^{13}$ Hz onto a sample, the system comprising:

(a) a substrate, said substrate having a surface side and a backside, (b) at least two spaced apart electrodes on the surface of said substrate defining a THz emitter gap in the space therebetween, (c) means for creating a DC field between said spaced apart electrodes, (d) optical pump means comprising a pulsed laser with the output beam of the pulsed laser incident on said emitter gap, thereby generating a THz radiation beam that is emitted from the emitter gap on the surface of the substrate, (e) sample mounting means for mounting a sample in the path of said THz radiation beam, the system characterized in that said substrate consists of a first material that is substantially transparent to the output beam of the optical pump means, and a second material overlying the first material, said second material being photoconductive and substantially absorbing the output beam of the optical pump means, said output beam of the optical pump means being incident on the backside of said substrate, and transmitted through said substrate to said emitter gap, the system further characterized in that sample mounting means is adapted to mount said sample in near field proximity to the said emitter gap.

2. The device of claim 1 in which the second material is a semiconductor.

3. The device of claim 2 in which the optical pump means comprises a pulsed laser with a pulse duration of 10 picoseconds or less.

4. The device of claim 2 further including means for collimating output radiation from the said sample.

5. The device of claim 2 in which the space between the emitter gap and the sample is void space.

6. The device of claim 5 wherein the output beam of the pulsed laser is incident on said emitter gap through an optical fiber.

7. The device of claim 2 in which the DC field is in the range of 1–100 volts.

8. The system of claim 1 in which the first material of the substrate comprises sapphire and the second material of the substrate comprises silicon.

9. The system of claim 8 in which the output beam has a wavelength in the range 0.4–0.9 microns.

10. A system for imaging far infra-red pulsed THz radiation in the pulse frequency range of $10^{10}$ to $10^{13}$ Hz onto a sample, the system comprising:

(a) a substrate, (b) at least two spaced apart electrodes on the surface of said substrate defining a THz emitter gap in the space therebetween, (c) means for creating a DC field between said spaced apart electrodes, (d) optical pump means comprising a pulsed laser, with the output beam of the pulsed laser incident on said emitter gap, thereby generating a THz radiation beam which radiates from said emitter gap through said substrate and is emitted from the backside of said substrate, (e) sample mounting means for mounting the sample in the path of said radiation beam, the system characterized in that said substrate has a thickness substantially less than the wavelength of said THz radiation, and the sample mounting means is adapted to mount the sample adjacent to the backside of said substrate in the path of said THz radiation beam and in near field proximity to said emitter gap.

11. The system of claim 10 in which the substrate comprises GaAs.

12. The system of claim 10 further including a blocking layer comprising a material that is substantially opaque to said THz radiation, said blocking layer covering at least that portion of the backside of the substrate in the path of said THz beam, said blocking layer having a pinhole located in the path of said THz beam, the pinhole having a diameter substantially less than the far field wavelength of the THz beam.

13. The system of claim 12 in which the diameter of the pinhole is less than 100 microns.

14. The system of claim 10 in which the thickness of the substrate is less than 200 microns.

* * * * *